US006816257B2

(12) United States Patent
Goix

(10) Patent No.: US 6,816,257 B2
(45) Date of Patent: Nov. 9, 2004

(54) METHOD AND APPARATUS FOR DETECTING MICROPARTICLES IN FLUID SAMPLES

(75) Inventor: Philippe J. Goix, Oakland, CA (US)

(73) Assignee: Guava Technologies, Inc., Hayward, CA (US)

( * ) Notice: Subject to any disclaimer, the term of this patent is extended or adjusted under 35 U.S.C. 154(b) by 0 days.

(21) Appl. No.: 10/652,665

(22) Filed: Aug. 28, 2003

(65) Prior Publication Data

US 2004/0036870 A1 Feb. 26, 2004

Related U.S. Application Data

(63) Continuation of application No. 09/600,021, filed as application No. PCT/US98/11958 on Jun. 9, 1998, now Pat. No. 6,710,871.
(60) Provisional application No. 60/049,212, filed on Jun. 9, 1997.

(51) Int. Cl.[7] .............................................. G01N 21/64
(52) U.S. Cl. ..................... 356/318; 250/458.1
(58) Field of Search ................. 356/317, 318, 356/417; 250/458.1, 459.1, 461.1, 461.2

(56) References Cited

U.S. PATENT DOCUMENTS

| 4,243,318 A | 1/1981 | Stohr ........................ 356/39 |
| 4,662,742 A | 5/1987 | Chupp ....................... 356/39 |
| 4,668,868 A | 5/1987 | Noller ..................... 250/458.1 |
| 4,790,653 A | 12/1988 | North, Jr. .................... 356/73 |
| 4,979,824 A | 12/1990 | Mathies et al. ............. 356/318 |
| 5,135,302 A | 8/1992 | Hirako ....................... 356/73 |
| 5,315,122 A | 5/1994 | Pinsky et al. ............ 250/461.2 |
| 5,317,162 A | 5/1994 | Pinsky et al. ............ 250/461.2 |
| 5,351,118 A | 9/1994 | Spinell ........................ 356/72 |
| 5,528,045 A | 6/1996 | Hoffman et al. ......... 250/458.1 |
| 5,682,038 A | 10/1997 | Hoffman .................. 250/458.1 |
| 5,739,902 A | * 4/1998 | Gjelsnes et al. ............. 356/73 |
| 5,842,150 A | * 11/1998 | Renberg et al. ............... 702/23 |
| 5,880,474 A | 3/1999 | Norton et al. ........... 250/458.1 |
| 5,962,238 A | 10/1999 | Sizto et al. ................ 435/7.24 |
| 6,020,209 A | * 2/2000 | Narang et al. .............. 436/514 |

FOREIGN PATENT DOCUMENTS

| EP | 0121261 | 10/1984 |
| EP | 0177813 | 4/1986 |
| EP | 0289976 | 5/1988 |
| GB | 2032097 | 7/1979 |
| JP | 5-312811 | * 11/1993 |
| WO | WO96/12963 | 5/1996 |

OTHER PUBLICATIONS

PCT International Search Report.

* cited by examiner

*Primary Examiner*—F. L. Evans
(74) *Attorney, Agent, or Firm*—Dorsey & Whitney LLP

(57) ABSTRACT

A method and apparatus for detecting a fluorescent substance tagged to a microparticle are described. The device comprises a single capillary flow carrier system for transporting the microparticle past a selected location, a source of electromagnetic radiation for irradiating the substance tagged to the microparticle, and a detection system for measuring fluorescent light emitted from the substance at the selected location. The method comprises transporting the microparticle to a selected location, irradiating a fluorescent substance tagged to the microparticle, and measuring the fluorescent light emitted from the fluorescent substance at the selected location.

4 Claims, 14 Drawing Sheets

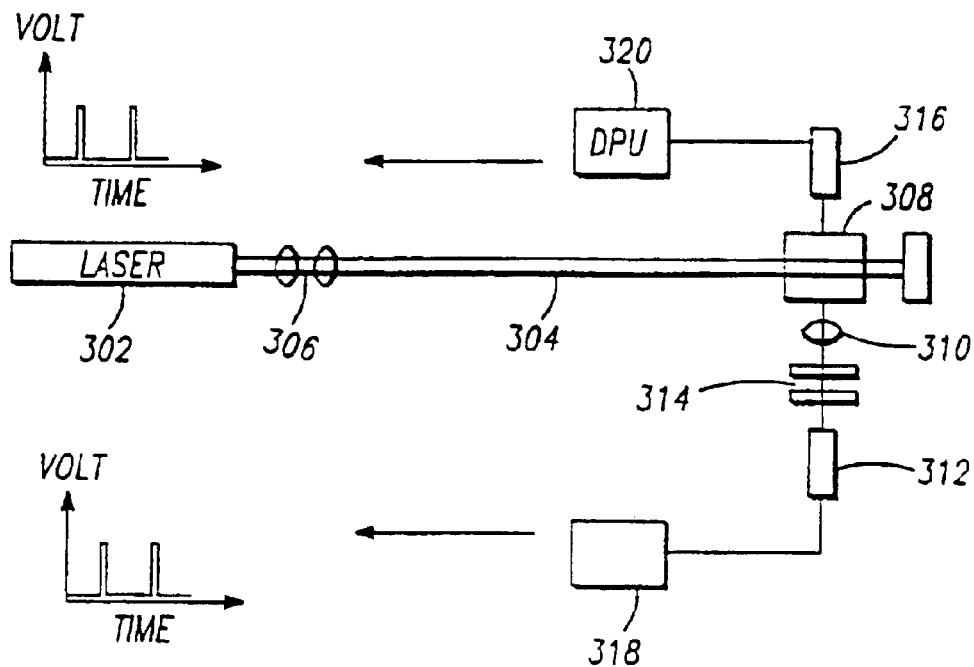
FIG.—3A
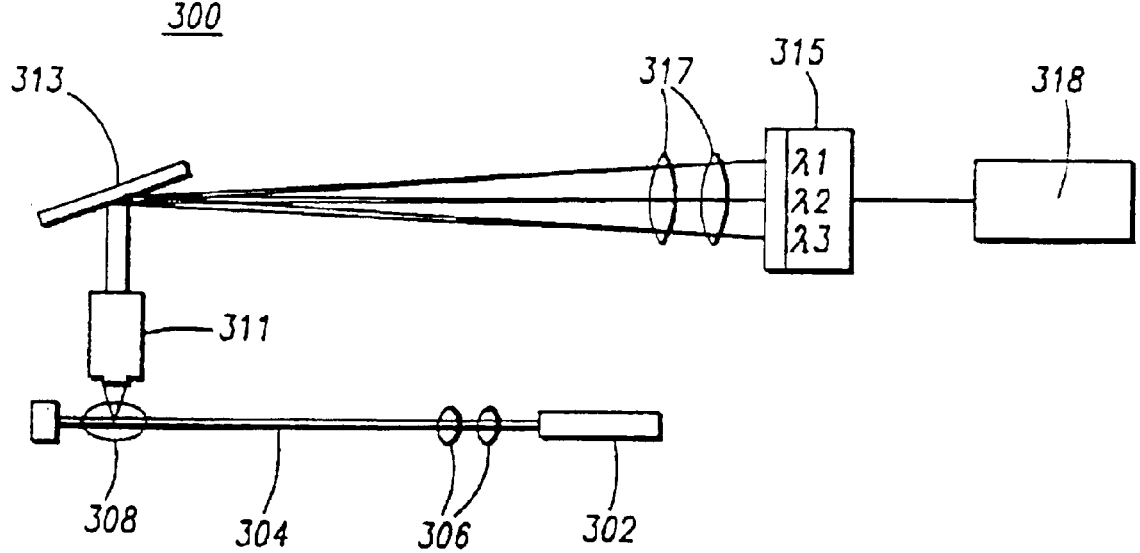
FIG.—3B

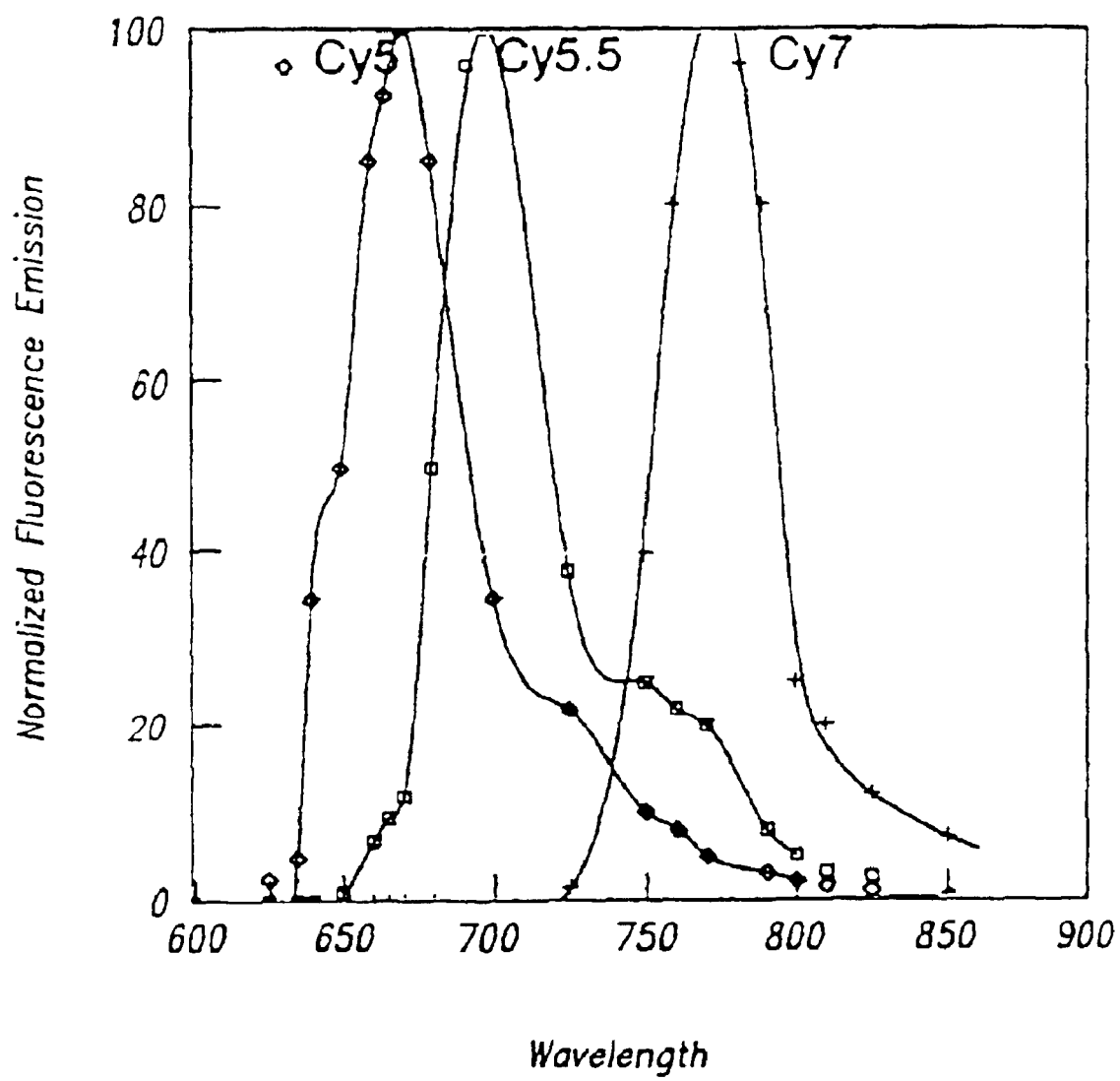
FIG.—5A

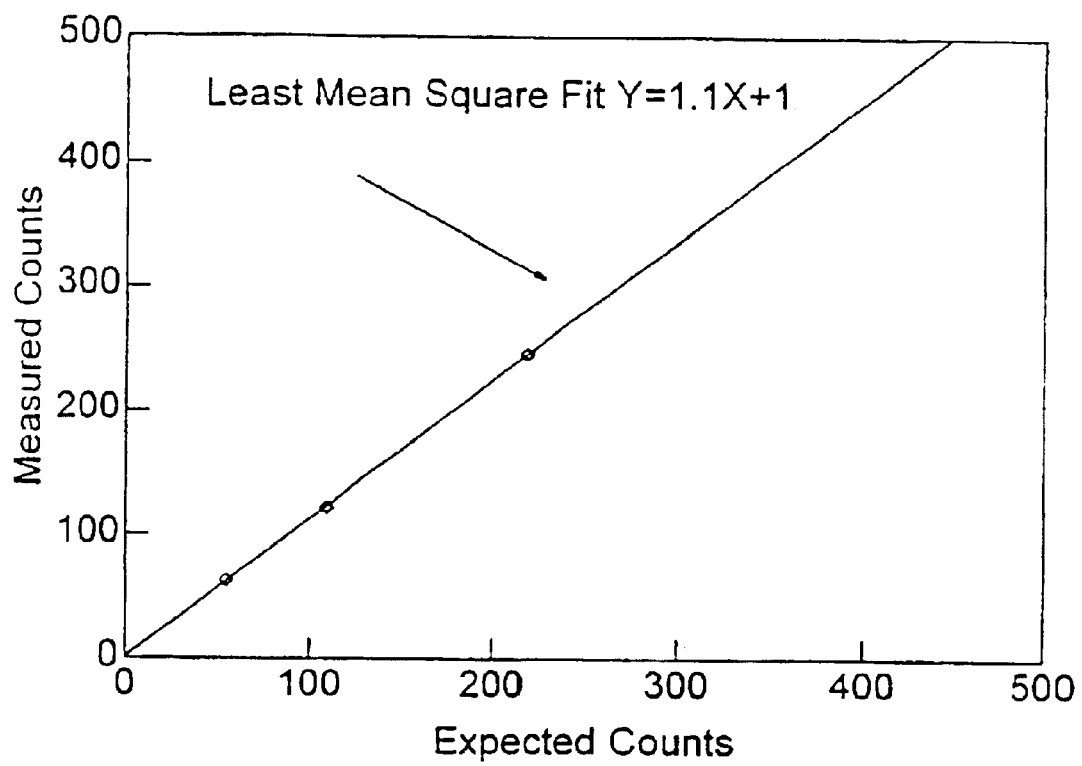
FIG.—6A

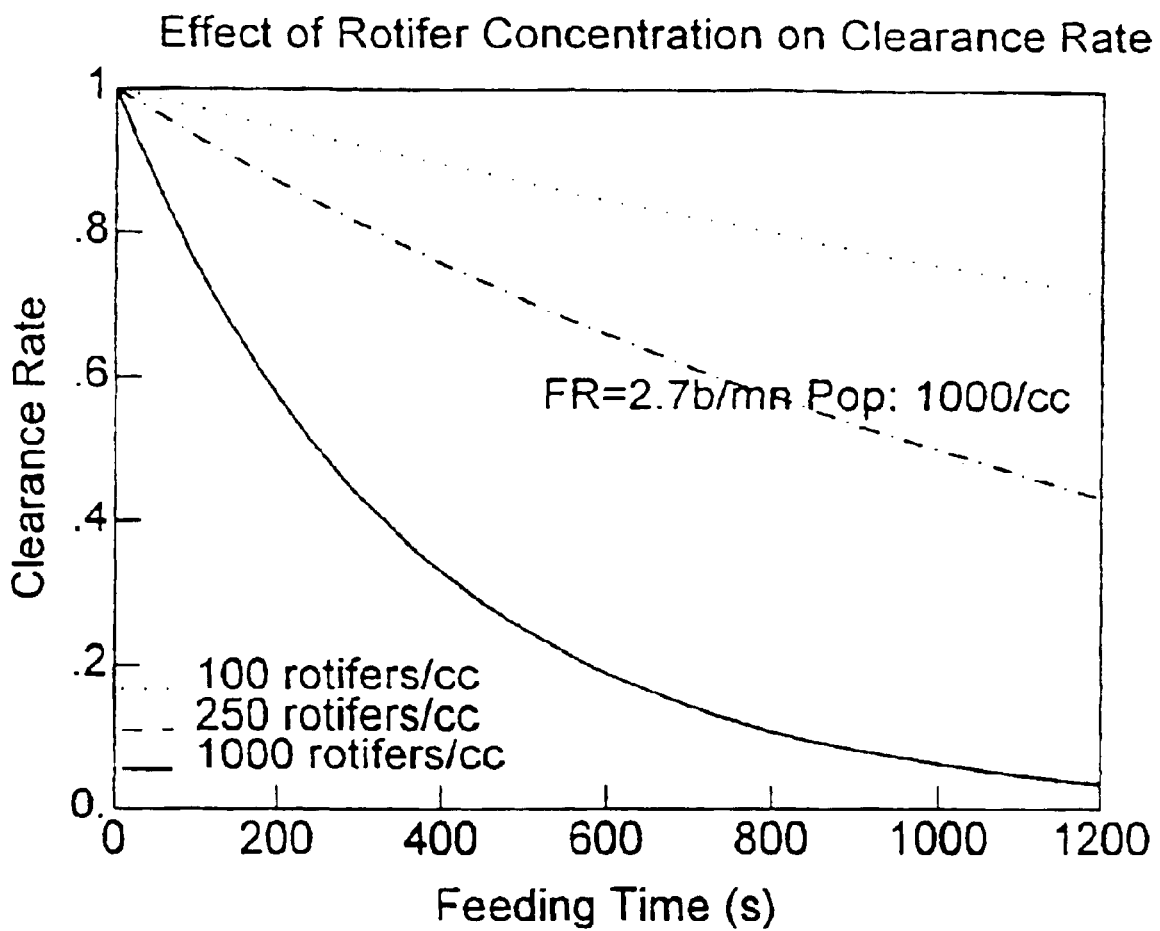
FIG. — 7A

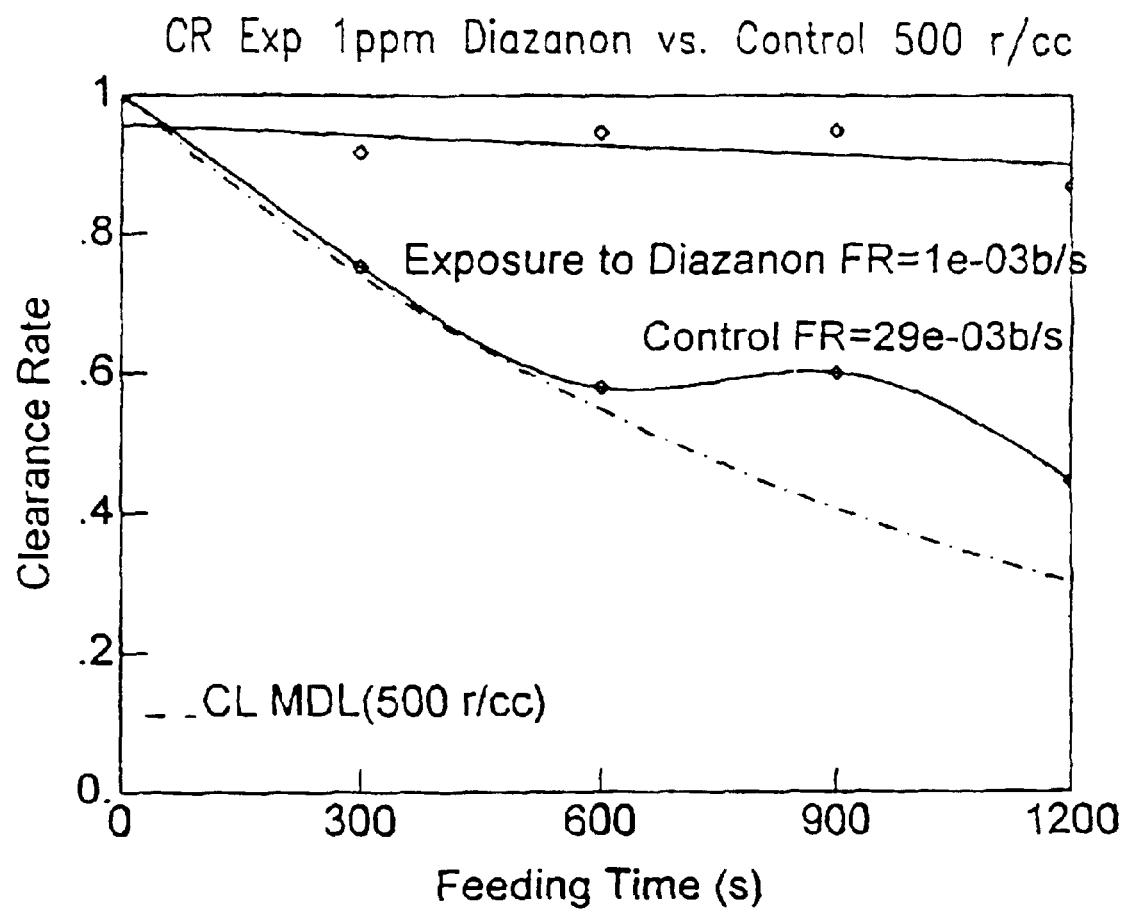
FIG.—7B

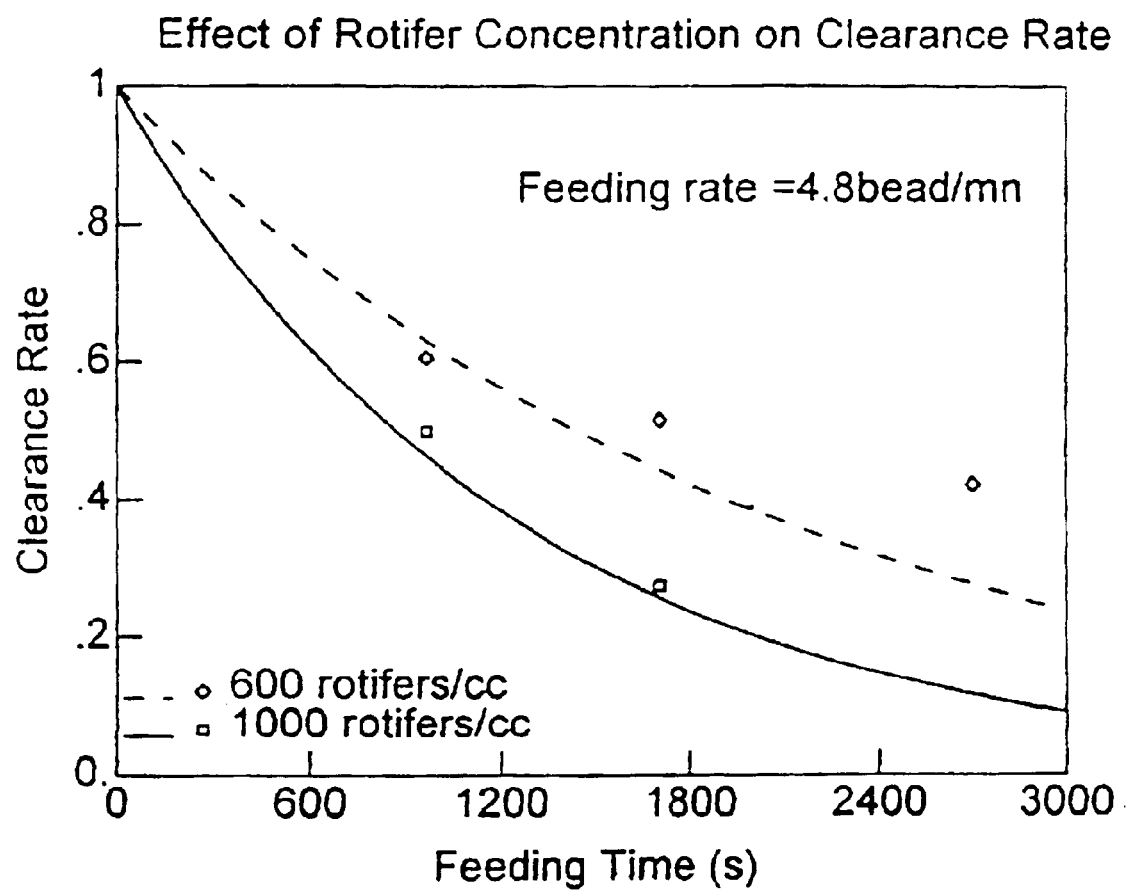
FIG.—7D

METHOD AND APPARATUS FOR DETECTING MICROPARTICLES IN FLUID SAMPLES

RELATED APPLICATION

This application is a continuation of prior application Serial No. 09/600,021 filed Jul. 7, 2002, now U.S. Pat. No. 6,710,871 issued Mar. 23, 2004, based upon PCT/US98/11958 filed Jun. 9, 1998, and provisional application No. 60/049,292 filed on Jun. 9, 1997.

BACKGROUND OF THE INVENTION

1. Field of the Invention

The present invention relates to a method and apparatus for detecting microparticles in fluid samples. More particularly, the present invention relates to a method and apparatus which uses a fluid delivery system and laser fluorescence detection system to detect fluorescently tagged microparticles in low concentrations in fluid samples.

2. Description of Related Art

Detection of microorganisms present at low concentration in fluids is critical to provide microbiological contamination answers faster to better treat patient diseases, to prevent deadly outbreaks, to better manage quality control processes in food, drink, and drug manufacturing plants, and to provide scientists with powerful and easy to use analytical research tools.

Testing methods for microorganisms such as *M. tuberculosis, Trichomonas vaginalis, Campylobacter, Salmonella, E. coli*, and *Cyclospora* include growth culture methods, PCR methods, fluorescently enhanced microscopic visualizations, ATP bioluminescence techniques, and bactometers. These methods are often slow and expensive, and have limited detection capabilities.

Testing devices include epifluorescent microscopes, fluorometers, and flow cytometers. Epifluorescent microscopes are coupled with cooled CCD high-resolution cameras to permit epifluorescent microscopic visualizations of microscopic particles. Fluorometers have limited detection capabilities, and is also not well suited when spectral differentiation in a large population of organisms is required. This is often the case when live versus dead organism differentiation is required. Flow cytometers can be very accurate in detecting and differentiating immuno-fluorescently dead or live labeled particles. However, flow cytometers are expensive and require an experienced technician or scientist to operate it and interpret the data.

*Cryptosporidium oocysts* and *Giardia* cysts may be detected using an immunofluorescent assay (IFA) procedure. This method uses polyclonal antibodies to stain the cysts which then can be detected by epifluorescent microscopy. This method is extremely labor-intensive, considering the number of particles to be investigated under the epifluorescent microscope by an experienced technician. Flow cytometeters may also be used, but they are very expensive and require an experienced and well-trained technician to operate. Furthermore, flow cytometers still require microscopy confirmation of oocyst identification.

Water quality monitoring is vital for managing supplies of unpolluted water for agriculture, industry, and human consumption. Water quality monitoring may be performed using test organisms as indicators of freshwater toxicity, for example, the fathead minnow *Pimephales promelas*, the cladoceran *Ceriodaphnia dubia*, and the green alga *Selenastrum capricornutum*. Test organisms are cultured under standard conditions, and exposed for a period of time to toxicants. Comparison of survival and reproduction rates of test organisms to control organisms provides an indication of water toxicity.

Bacteria enzyme activity may be used to assess water quality by using a specially designed enzyme substrate that becomes fluorescent when cleaved. This substrate is cleaved by enzymes in the bacteria and emits fluorescence light when exposed to light of the proper wavelength. The rate of enzyme activity can be measured using a fluorometer, and provides an indirect measurement of the level of toxicant stress on the bacteria.

Zooplankton feeding behavior may also be used to assess water quality. Extensive acute toxicity studies have been performed using plankton, in general, and various species of rotifer, in particular. Rotifer feeding and reproduction rates can be used as a rapid toxicity assessment tool. The effect of a wide range of chemicals including xylene, cadmium, copper, mercury, and diazanon on the feeding and reproduction rates of the rotifer *Brachionus calyciflorus* for fresh water and *Brachionus plicatilis* for marine waters has been extensively studied. In the feeding rate method, the rotifers are exposed for several minutes to water containing a toxicant, and then allowed to feed on fluorescently labeled beads. The rotifers are then anesthetized, washed, transferred to a microscope slide, and individually examined using a fluorescent microscope. The feeding rate is estimated by quantifying the intensity of fluorescence of ingested beads in the digestive tract of individual rotifers using an imaging technique. This method requires a trained operator, a camera, and a fluorescent microscope, which makes it slow and expensive.

What is needed are methods and apparatus for detecting microparticles such as harmful microorganisms and assessing water quality which is rapid, sensitive, reproducible, substantially automatic, and cost-effective.

SUMMARY OF THE INVENTION

The present invention is a device for detecting a fluorescent substance tagged to a microparticle. The device comprises a single capillary flow carrier system for transporting the microparticle past a selected location, a source of electromagnetic radiation for irradiating the substance tagged to the microparticle, and a detection system for measuring fluorescent light emitted from the substance at the selected location.

BRIEF DESCRIPTION OF THE FIGURES

FIG. 3A shows one embodiment of a laser fluorescent measurement setup.

FIG. 3B shows another embodiment of a laser fluorescent measurement setup

FIG. 5A shows the emission spectra for various fluorescent cyanide dyes used to tag microparticles.

FIG. 6A shows a calibration curve obtained with water sample seeded with known amount of 2 µm fluospheres using the device of the present invention.

FIG. 7A shows normalized bead concentrations versus feeding time according to an analytical model for three different organism concentrations.

FIG. 7B shows normalized fluosphere concentrations versus feeding time for a test sample containing 1 ppm of diazanon and a control sample, using a rotifer concentration of 500 rotifers/ml.

FIG. 7D shows normalized fluosphere concentrations versus feeding time for a 600 rotifers/ml sample and an 1000 rotifers/ml sample.

DETAILED DESCRIPTION OF THE INVENTION

Figure 1:
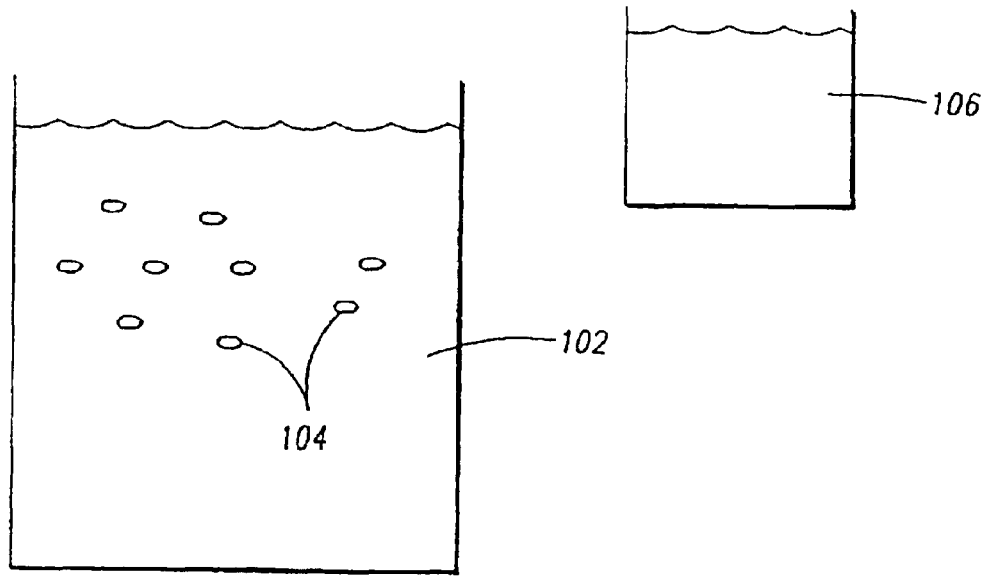
FIG. 1 shows a sample preparation system.

FIG. 1 shows a sample preparation system 100. Sample preparation system 100 contains a fluid sample 102 suspected of containing microparticles 104. Fluid sample 102 may be run through a filter or trap to separate out any unwanted or macroscopic particulate matter. In order to prepare a sample to be tested, a fluorescent substance 106 is allowed to react with fluid sample 102 and microparticles 104. Fluorescent substance 106 may be one or more fluorescent stains, dyes, or reagents designed to stain, tag, or otherwise attach themselves to microparticles 104. A test sample 108 is obtained by filtering out any free remaining fluorescent substance 106 from fluid sample 102. Test sample 108 thus contains fluid sample 102 and fluorescent substance 106 attached to microparticles 104.

Fluid sample 102 may be a water sample, urine sample, blood sample, food product sample, or any other fluid to be tested. Fluid sample 102 may contain PCR-amplified samples for detection of viruses such as HIV. Microparticles 104 may be *M. tuberculosis, Trichomonas vaginalis, Campylobacter, Salmonella, E. coli, Cyclospora, Cryptosporidium* oocysts, *Giardia* cysts, or any other bacterium, virus, fungus, or microorganism that is capable of being tagged. Microparticles 104 may also be CD4 or CD8 cells for monitoring of AIDS patients. Different fluorescent substances 106 may be used with microparticles 104 to allow different types of microorganisms to be detected and distinguished from each other. For example, for bacteria, fluorescent substance 106 can be standard DNA or surface-label-reagent stains. For *Cryptosporidium* oocysts or *Giardia* cysts, fluorescent substance 106 can be a fluorescent dye conjugated with anti-Cryptosporidium or anti-Giardia antibodies, respectively. Fluorescent substance 106 may also be magnetically charged so that it can be affected by a magnetic field.

Microparticles 104 may also be microscopic beads containing a fluorescent substance 106. To measure the concentration of a toxicant in fluid sample 102, filtro-feeder microorganisms such as rotifers or zooplankton may be added to fluid sample 102 in known quantities. Such filtro-feeder microorganisms have a feeding rate which is a well-known function of toxicant concentration. After a known incubation period, microparticles 104 are added to fluid sample 102. Microparticles 104 may be fluospheres capable of being ingested by the filtro-feeder organisms, such as latex beads containing a fluorescent dye available from Molecular Probes, Inc., Eugene, Oreg. The fluospheres may have a uniform diameter of 2 µm or have non-uniform sizes. They may have uniform spectro-photometric properties, with a maximum absorption wavelength of 624 nm, and a maximum emission wavelength of 645 nm, or have varying spectro-photometric properties. At known intervals of time, a test sample 108 is drawn from sample preparation system 100. Test sample 108 is obtained by filtering out any uningested microparticles 104 from fluid sample 102. Test sample 108 thus contains water sample 102 and organisms 104 with microparticles 104 in their digestive tracts.

Figure 2A:
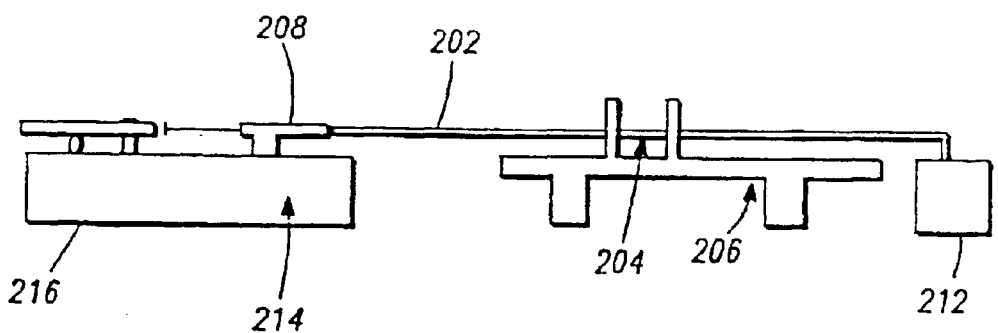
FIG. 2A shows a flow carrier system.

FIG. 2A shows a flow carrier system 200. Flow carrier system 200 is a fluid delivery system which introduces test sample 108 into a capillary tube 202. Capillary tube 202 may have very thin walls and excellent optical properties. Capillary tube 202 may have an internal diameter configured to admit microparticles 104 one at a time. A section of capillary tube 202 defines a test volume 204. Capillary tube 202 may be at least partially coupled to an optical table 206, which serves to hold capillary tube 202 in place. Multiple capillary tubes 202 may be arranged in parallel to obtain higher throughputs.

Flow carrier system 200 may include a pump system 216 coupled to capillary tube 202. Pump system 216 may be a syringe 208 which contains test sample 108, and injects test sample 108 through capillary tube 202 and test volume 204. After passing through capillary tube 202, sample 108 may pass into a dump 212. In this manner, microparticles 104 in test sample 102 may be passed one at a time through capillary tube 202. Pump system 216 may further include a syringe pump 214 coupled to syringe 208. Syringe pump 214 is configured for precise control of flow of test sample 108 through capillary tube 202. Pump system 216 may also be a peristaltic pump.

Figure 2B:
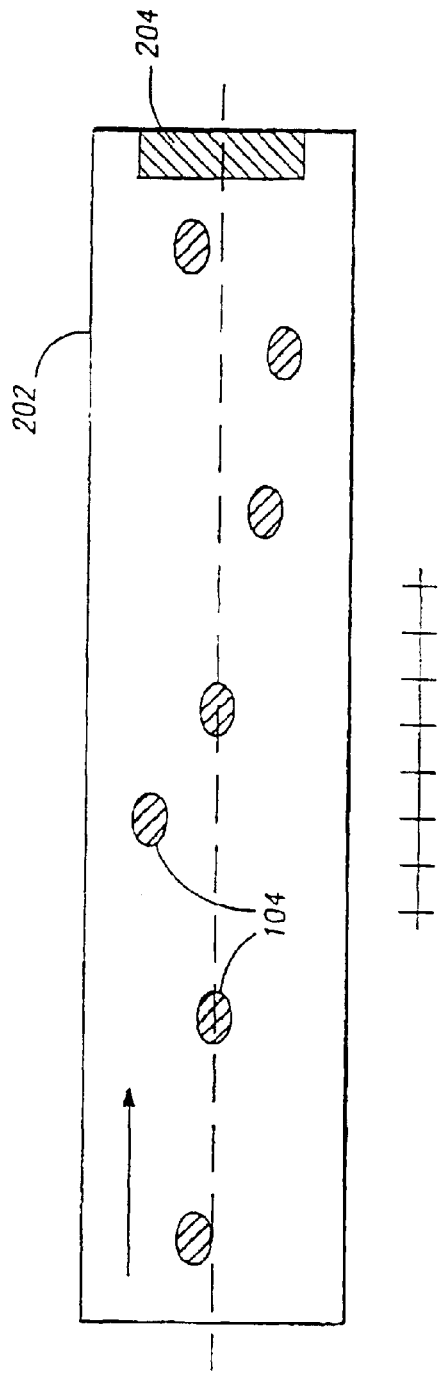
FIGS. 2B and 2C show detailed views of two embodiments of the capillary tube.
Figure 2C:
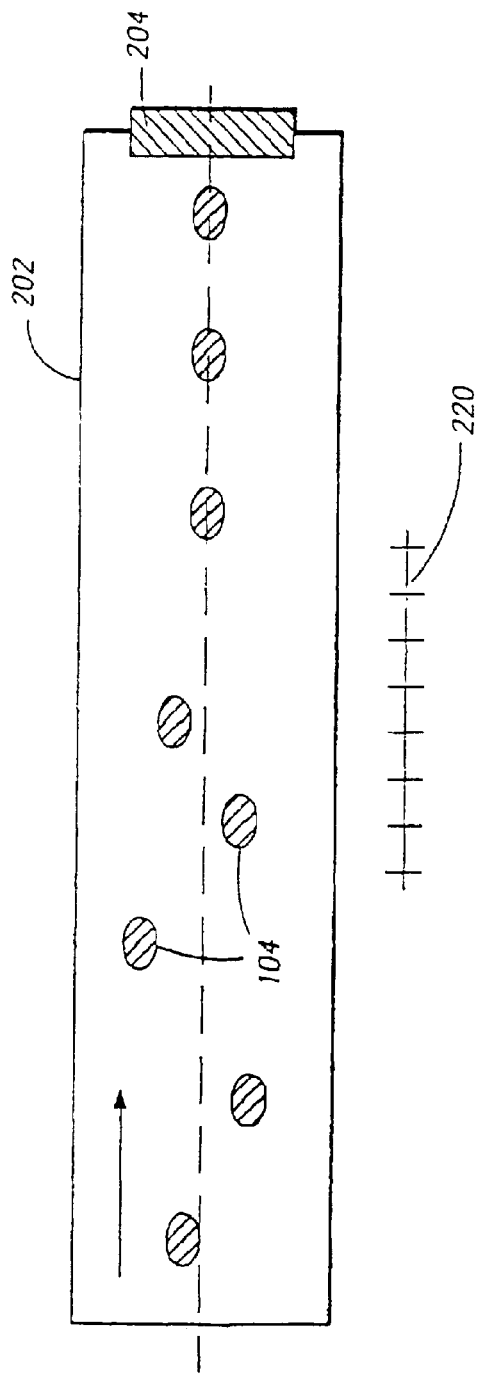

FIGS. 2B and 2C show detailed views of two embodiments of capillary tube 202. FIG. 2B shows microparticles 104 flowing through capillary tube 202 towards test volume 204. FIG. 2C shows capillary tube 202 with a magnetic element 220 positioned in a concentric fashion around capillary tube 202. Magnetic element 220 may be a continuous ring, or be comprised of one or more separate elements. Magnetic element 220 may be used in conjunction with microparticles 104 and fluorescent substance 106 which are magnetically charged. This configuration may assist in substantially focusing microparticles 104 tagged with fluorescent substance 106 to the center of capillary tube 202 as they flow through test volume 204, thus improving detection of microparticles 104.

FIG. 3A shows a laser fluorescent measurement setup 300. A laser 302 generates a laser beam 304. Laser beam 304 may be focused through one or more lenses 306 onto test volume 204. The wavelength and beam size of laser 302 is selected according to the absorption wavelength of fluorescent substance 106 and the size of capillary tube 202.

When test sample 108 is passed through test volume 204, any fluorescent substance 106 present in test sample 108 is exposed to laser beam 302. Alternatively, a standing test sample 108 in capillary tube 202 may be moved relative to laser beam 302 to expose test sample 108. A collecting lens 310 collects and images fluorescence light emitted by fluorescent substance 106 onto a photo-multiplier 312. A set of interference filters 314 may be placed in front of photo-multiplier 312 to filter out the resonant light from the fluorescence light. A photodiode 316 may be placed on the opposite side of test chamber 308 to collect the resonant light. Output from photo-multiplier 312 may be sent to a first digital processing unit 318 to analyze fluorescence peaks. Output from photodiode 316 may be sent to a second digital processing unit 320 to analyze Mie scattering peaks.

FIG. 3B shows another laser fluorescent measurement setup 300. In this case, the fluorescence emissions pass through a diffraction grating 313 and are imaged onto a multiple detector array 315. The focal length and aperture of collecting lens 310, the dispersion characteristics of grating 313, and the size and separation of the multiple detectors in array 315 are optimized to detect at least two or three fluorescent emission bands specific to the emission spectrum of fluorescent substance 106 as well as resonant light. A set of interference filters 317 may be used to single out the fluorescence emission of fluorescent substance 106 used to tag microparticles 104. By reading the fluorescence emission at multiple spectral locations using multiple interferential filters 317 with specific transmission characteristics, the particular fluorescent substance 106 used can be detected and distinguished. The contribution of the total fluorescence signal to each detector will provide the data needed to differentiate the particular fluorescent substance 106 from the fluorescence emissions of non-tagged particles. Output from multiple detector array 315 may be fed to a digital processing unit 318, which processes and digitizes the multiple signals delivered by multiple detector array 315.

Figure 3C:
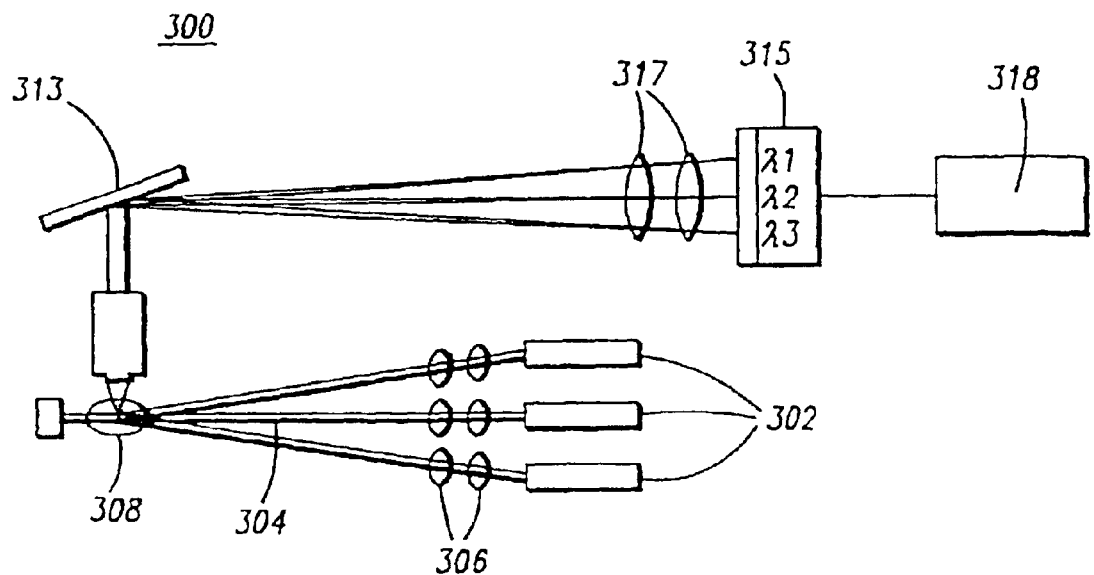
FIG. 3C shows yet another embodiment of a laser fluorescent measurement setup

FIG. 3C shows another embodiment of a laser fluorescent measurement setup 300 A plurality of lasers 302 generates a plurality of laser beams 304. Laser beams 304 may be focused through one or more lenses 306 onto test volume 204. The size of laser beam 304 may be matched to the size of capillary tube 202. The wavelengths of lasers 302 are tuned to specific absorption bands of fluorescent substance 106. This multiple laser and detection system may assist in reducing false positive and negative results associated with a single laser system.

Figure 4A:
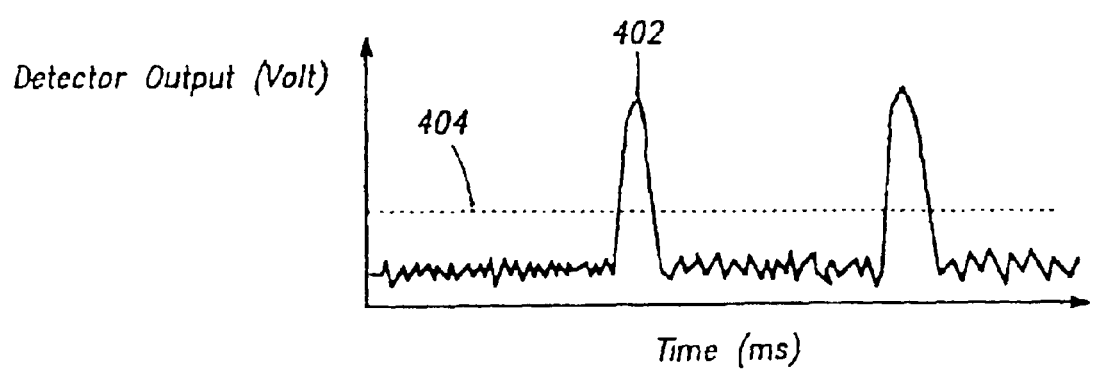
FIG. 4A shows a sample output of a digital processing unit.

FIG. 4A shows a sample output from digital processing unit 318. The voltage signal coming out of photo-multiplier 312 is digitized and transferred to a computer where it can be manipulated and analyzed. The voltage signal may be digitized at a frequency of up to 3000 Hz with 8-bit precision.

Every time fluorescent substance 106 passes through test volume 204, a fluorescence peak 402 is created. A threshold value 404 may be selected according to the baseline signal level and its variance. The number of fluorescence peaks 402 detected above threshold value 404, along with the size of voltage spikes, give a measurement of the amount of fluorescent substance 106. In the case of toxicant concentration, comparing this data with the data for an uncontaminated control sample permits determination of the toxicant concentration in water sample 102.

Figure 4B:
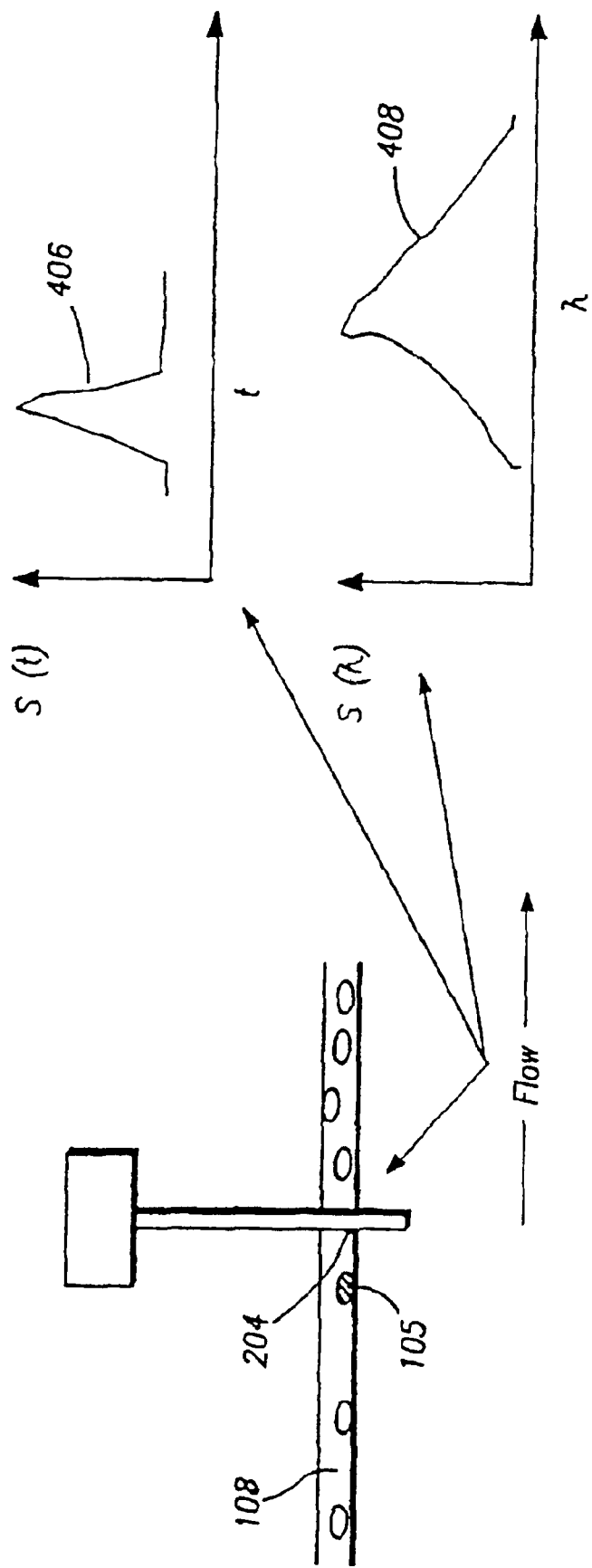
FIG. 4B shows another sample output of a digital processing unit.

FIG. 4B shows another sample output from digital processing unit 318. When an microparticle 104 which has been tagged by fluorescent substance 106 passes through test volume 204, the it generates a burst of fluorescence light with a time signature 406 and spectral signature 408 The time signature 406 and spectral signature 408 is then processed by the digital signal processing unit 318 and compared with the expected time and spectral signatures of microparticle 104 and fluorescent substance 106 to be detected.

Because a wide range of particles and organisms naturally fluoresce at a wide range of wavelengths, it is crucial to spectrally differentiate an microparticle to reliably detect it. Multiple laser sources and detectors may be used in close wavelength proximity to spectrally pinpoint the fluorescence pattern of the dye attached to the microparticle targeted for detection. The electronic signal analysis techniques can be tailored to the understanding of the pre-defined shape and spectral properties of the target microparticle prior to detection.

The use of multiple signals provides normalization and improved selectivity. Measurements at more than one fluorescence emission wavelength and/or at more than one excitation wavelength give spectral selectivity which can distinguish different dye sources. Because the dyes used for immunofluorescence commonly have relatively narrow emission peaks compared to background fluorescence sources, ratios of on-peak to off-peak signals may reliably distinguish dye-labeled particles from background events of similar absolute fluorescence.

Background particle signals are rejected through the use of electronic filtering, thereby allowing a sustained and very high sampling data rate. Electronic filtering involves the use of several detectors and is made possible by the uniqueness of a particle's light scattering signature and the presence of at least two fluorescent wavelength signatures. Based on the differential signal analysis of each of the detected log amplified signals, the capability of singling out the tagged microparticle at a data frequency rate of up to 50 kHz can be achieved.

FIG. 5A shows emission spectra of various fluorescent cyanide dyes which may be used to tag microparticles 104: Cy5, Cy5.5, and Cy7, with maximum absorption peaks of 650 nm, 675 nm, and 743 nm, respectively. Multiple detector array 318 may be used to first record the fluorescent spectrum of the particular dye. The fluorescent spectra emitted by the tagged microparticles 104 in the sample is then compared to the recorded fluorescent spectrum of the dye. In this fashion, tagged microparticles 104 can be identified and distinguished from other fluorescently tagged microparticles 104. In addition, because the flow rate is controlled, the width of the trace signal can be considered proportional to the diameter of microparticle 104 crossing test volume 204.

Figure 5B:
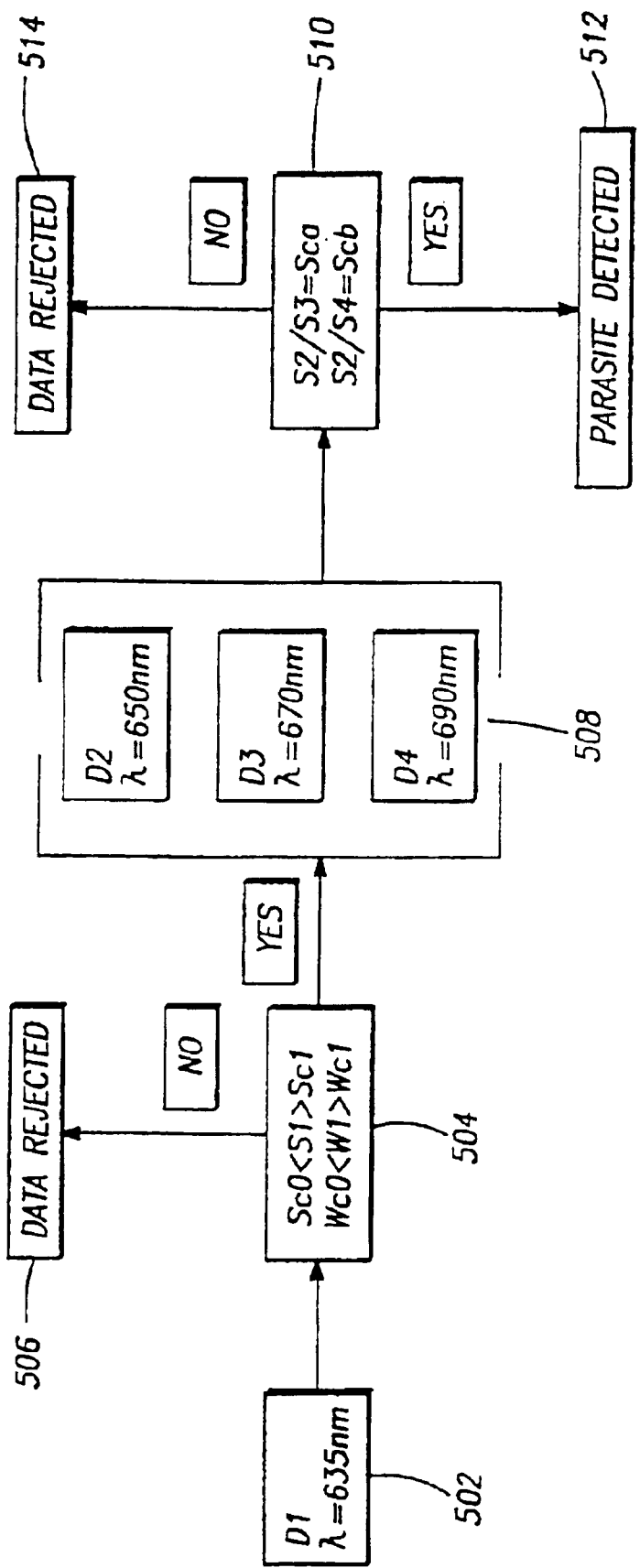
FIG. 5B shows a flowchart of a signal processing strategy to detect a Cy5 tagged microparticle in the presence of other fluorescently labeled microparticles.

FIG. 5B shows a flowchart of a signal processing strategy to detect a Cy5 tagged microparticle 104 in the presence of other fluorescently labeled microparticles. Four detectors are used. Detector D1 is centered on the resonant laser excitation, in this case 635 nm. Detectors D2, D3, and D4 are centered at 650 nm, 670 nm, and 690 nm, corresponding to features of the Cy5 fluorescence emission.

When a microparticle 104 is detected in test volume 204, first, the time trace of the signal detected by detector D1 is analyzed (block 502) and the signal intensity S1 and the pulse width W1 are compared with the expected time trace (Sc, Wc) generated by the passage of the particular microparticle in the test volume (block 504). If the detected signal does not meet this criteria, then the data is rejected (block 506). If the detected signal passes this first test, then the fluorescence intensity ratio of the detectors D2, D3, and D4 are analyzed (block 508). The fluorescent ratio of S2/S3 and S2/S4 are compared with the expected fluorescence ratios corresponding to the Cy5 fluorescence spectra Sca and Scb, respectively (block 510). If these two tests are positive, a microparticle is counted (block 512); if the tests are negative the data is rejected (block 514).

EXAMPLE 1

Flow carrier system 100 was calibrated using water samples with known fluosphere concentrations. A reference solution of $3 \times 10^9$ beads/ml was diluted 1000 times. Then water samples containing 0, 3, 500, 7000, 14000 and 28000 beads/ml were prepared with a 10% confidence interval using a 20 $\mu$l micropipet. These water samples were passed through the device. FIG. 6A shows detected fluorescence peak counts versus expected counts for the calibration samples. An excellent correlation was consistently obtained.

A reference sample of $10^7$ *E. coli* SYTO™ 60 DNA-stained was prepared by first killing the bacteria using a 70% isopropanol exposure for one hour and then following with three sterile washes. The *E. coli* bacteria population was then stained with a 5 $\mu$mol concentration SYTO™ 60 dye. The spectral characteristics of the SYTO™ 60 dye (Abs=650 nm, Em=678 nm) are very well suited for the laser-based system of the present invention.

Five graded concentration samples from $10^7$ to 0 *E. coli* per ml stained were prepared using a 20 $\mu$l micropipette and 2 $\mu$m filtered de-ionized water. A 100 $\mu$l solution of each sample was drawn using a 1 ml syringe. The syringe was placed onto a syringe pump, and a 10 $\mu$l/min flow rate of the solution was injected into a 70 $\mu$m single capillary towards the test volume. The fluorescent test volume was defined by a 20 $\mu$m focused laser beam using a 635 nm, 5 mW laser diode and a single 10 mm focal lens. The test volume was imaged onto a 3 mm×3 mm slit using a 40× objective microscope. The photodetector signal was digitized at 3000 Hz and 8 byte dynamic range. The digitized signal was transmitted through a single serial cable onto a laptop computer. The signal was displayed on-line on a window screen using proprietary software. A time series corresponding to an injection of each sample at 10 $\mu$l/min flow rate during 30 sec was recorded. A triplicate experiment was performed for each sample, which corresponds to a 90 sec injection. By controlling the flow rate, the injection time, and the expected concentration, an expected fluorescent peak count was calculated and compared with the actual measured count. For each sample, the average peak residence time, peak intensity, and peak power (peak integral) were also computed.

The arrival process of the particle across the test volume was assumed to follow a random arrival process and therefore follow a Poisson process. The expected count number was corrected accordingly, to take into account the probability of having more than one particle arriving into the test volume during a time window equivalent to the particle transit time across the laser beam, taking into account the fact that a single detected count could be attributed to more than one particle.

Figure 6B:
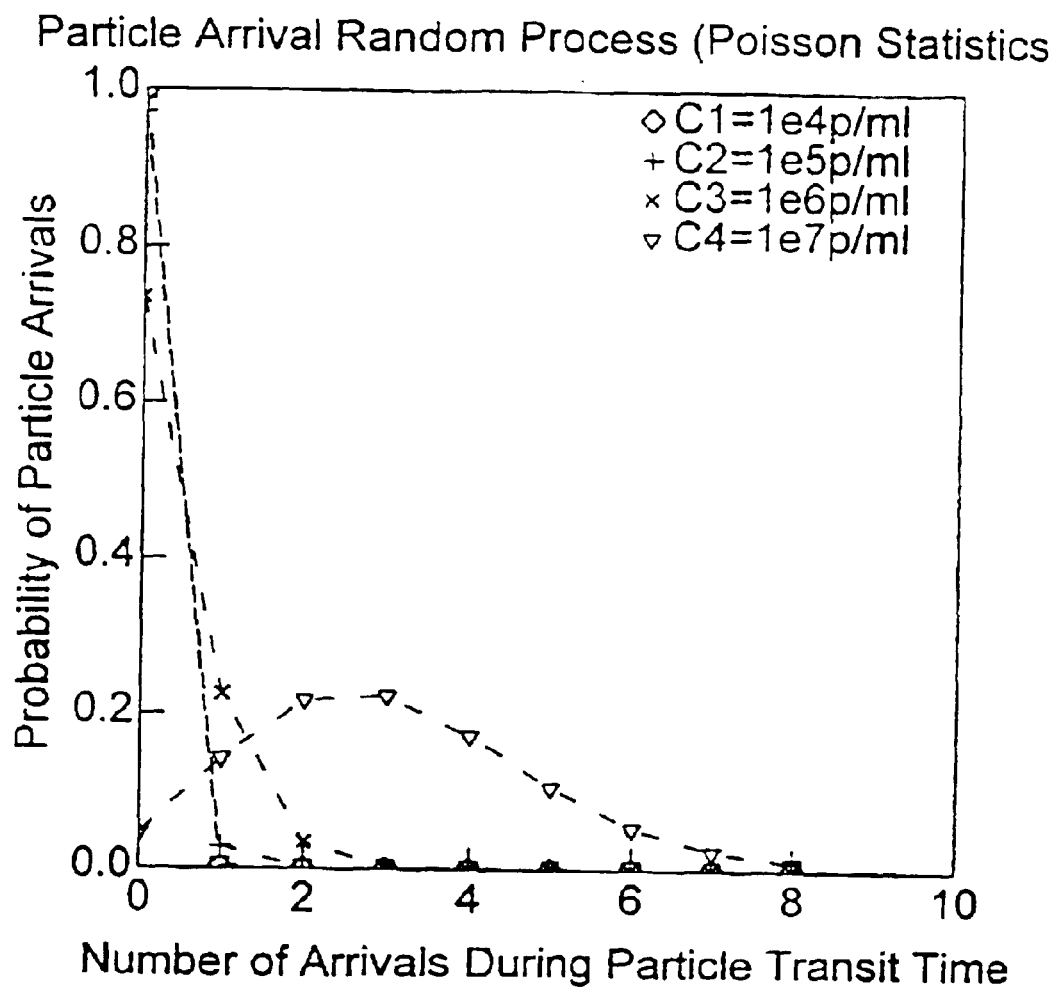
FIG. 6B shows a graph of the dependence of the particle concentration on the particle arrival rate distributions (Poisson statistical model).

FIG. 6B represents the particle arrival rate distribution at the test volume for the organism concentration investigated. For concentrations greater than $10^5$ p/ml at a 10 $\mu$l/min flow rate, a Poisson statistical correction is necessary. In particular, at a concentration of $10^7$ *E. coli* per ml, there is more than one *E. coli* crossing the test volume 80% of the time.

Figure 6C:
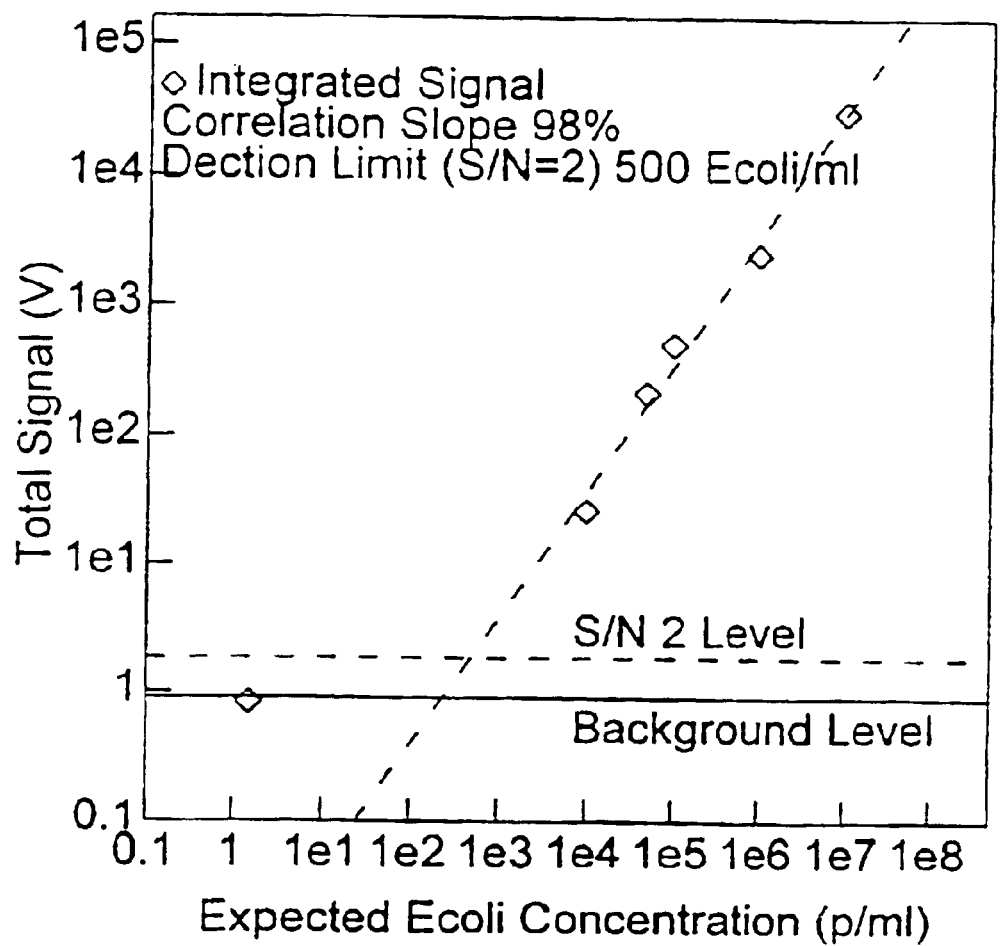
FIG. 6C shows a graph of the evolution of the integrated detected fluorescence signal versus the SYTO™ 60 *E. coli* concentration.

FIG. 6C represents a correlation between the expected concentration and the integrated detected fluorescence signal corresponding to the passage of individual stained *E. coli* through the laser test volume. The integrated signal was computed as the product of the number of detected peaks corrected by Poisson statistics, and the average peak power (V/ms). The correlation is excellent, with a 98% slope. However, when there was no *E. coli* present in the sample, an integrated background noise of 4 peaks every 30 seconds was detected. These background peaks where attributed to bubbles deflecting the beam reflection into the photodetector slit or to naturally fluorescent particles. The use of multiple wavelength detection arrays and a light scattering detector may eliminate these false positive counts.

EXAMPLE 2

Water quality monitoring using rotifers was performed using a capillary tube with an internal diameter of 70 $\mu$m, a narrow band, 635 nm, 3 mW diode laser with a beam diameter of 40 $\mu$m was used. Interference filters were selected to transmit 12% at 670 nm (20 nm FWM), and $10^{-6}$ at all other wavelengths.

Method

1. A live *B. plicatilis* rotifer culture was obtained from Aqua-Farms, Fla. These rotifers were chosen because they are easy to raise, and the influence of toxic samples on their feeding, reproduction, and death rates have been studied extensively. The average concentration of rotifers in a 100 ml vial was counted using five 20 $\mu$l samples examined under a 50× microscope. An average count of 10 rotifers per 20 $\mu$l sample was measured, or about 500 rotifers/ml.
2. Two samples of 8 ml each were used to make the feeding rate measurements, a reference sample and test sample. These two vials were filled with the 500 rotifers/ml reference solution.
3. A 2000 ppm diazanon solution was prepared using the rotifer medium solution, so as to maintain water quality parameters such as pH, $O_2$, alkalinity, salinity, and temperature as constant as possible. A 20 $\mu$l amount of the diazanon solution was added to test sample.
4. After a 5 minute incubation, 20 $\mu$l of a $40 \times 10^6$ beads/ml solution of crimson fluospheres was added to both the reference and test samples. The time was noted as t=0.
5. Using two identical syringes connected with a luer union to a 100 $\mu$m piece of nylon tubing terminated with a 20 $\mu$m plankton filter, a 50 $\mu$l sample was extracted from the reference and test samples. In both cases, the organisms were filtered out from the bead solution.
6. The reference and test samples were successively passed through the test chamber using the syringe pump at a flow rate of 15 $\mu$l/min. The data from data acquisition were stored for later analysis.
7. Steps 5 and 6 were repeated at t=5, 10, 15, and 20 minutes.

Data Analysis

Each data file was retrieved, using TOXANA™, a time series data analysis software program. This program allows visualization of the digitized photo-multiplier trace signal on a 0–5 V scale for each data file. An assessment of the signal baseline mean and variance values (where no peak is detected) was made for each file. From this measurement, a peak detection threshold, $T_d$, was computed as follows:

$$T_d = \text{mean} + 2\sqrt{\text{variance}}$$

The number of peaks with an intensity above $T_d$ were calculated for each file, as well as the average peak intensity, the average peak width, and the average peak area.

Analytical Model

The clearance volume $V_{Cl}$ for an organism with an average motility $\Omega$ and clearance diameter d can be assumed to be:

$$V_{Cl} = \Omega \cdot \pi \cdot \frac{d^2}{4} \quad \text{(Eq. 1)}$$

The number of beads present in the clearance volume per unit of time is equal to:

$$\frac{dN_b}{dt} = C_b(t) \cdot V_{Cl} \quad \text{(Eq. 2)}$$

Assume that a volume V contains organisms with an average motility $\Omega$. In this volume the concentration of food particles or beads is $C_b(t)$.

The change in bead concentration varies per unit of time:

$$C_b = \frac{d(C_b(t))}{dt} = -\frac{dN_b(t)}{dt} \cdot \frac{N_0}{V} \quad \text{(Eq. 3)}$$

By substituting (1) and (2) into (3), the rate at which the bead concentration varies with time is governed by the differential equation:

$$\frac{d(C_b(t))}{dt} = -C_b(t) \cdot \pi \cdot \frac{d^2}{4} \cdot \Omega \cdot \frac{N_0}{4} \quad \text{(Eq. 4)}$$

Define the constant K as:

$$K = \pi \cdot \frac{d^2}{4} \cdot \Omega \cdot \frac{N_0}{V} \quad \text{(Eq. 5)}$$

Then 1/K is a time constant which reflects the rate at which the bead concentration decreases. Then (5) becomes:

$$\frac{d(C_b(t))}{dt} = -K \cdot C_b(t) \quad \text{(Eq. 6)}$$

Integrating (6) gives:

$$C_b(t) = \lambda \cdot e^{-Kt} \quad \text{(Eq. 7)}$$

When t=0 and $C_N(t=0)=C_{B0}$, (7) becomes:

$$C_b(t) = C_{B0} \cdot e^{-Kt} \quad \text{(Eq. 8)}$$

The feeding rate is defined as the number of beads ingested per organism and per unit of time. It can be expressed by:

$$FR = \frac{dN_b}{dt} \cdot \frac{1}{N_0} = \frac{d(C_b)}{dt} \cdot \frac{V}{N_0} \quad \text{(Eq. 9)}$$

Combining (8) and (9), F can be expressed as follows:

$$FR = K \cdot C_b(t) \cdot \frac{V}{N_0} \quad \text{(Eq. 10)}$$

Assuming that $d(C_b)/dt$ is small compared with $C_b(t)$, F becomes a constant which can be expressed as:

$$FR = K \cdot C_b \cdot \frac{V}{N_0} \quad \text{(Eq. 11)}$$

FIG. 7A shows normalized bead concentrations versus feeding time according to the model given in Eq. 8 for three different organism concentrations: 100 rotifers/ml, 250 rotifers/ml, and 1000 rotifers/ml. The analytical value used to model the feeding rate (FR) in this case is 2.7 beads/min.

This value was computed based on the following assumptions: the organism is a rotifer and its clearance rate is proportional to a 150 $\mu$m diameter section with a motility of 15 cm/s. It is important to note that the sensitivity of the technique strongly depends strongly on the organism concentration.

Results

FIG. 7B shows normalized fluosphere concentrations versus feeding time for a test sample containing 1 ppm of diazanon and a control sample. To compare the experimental results to the model, a concentration of 500 rotifers/ml was used.

For the control sample the correlation between model and experiment is excellent for the first 600 seconds. In this region, the average feeding rate is $29 \times 10^{-3}$ beads/sec. The departure of experiment from the model after 900 seconds can be attributed to two factors. First, the model assumes that the variation of $C_b$ remains small compared to $C_b$ and therefore the feeding rate is a constant. In fact, the feeding rate depends on the food concentration, which after 900 seconds has dropped by 50%. This variation cannot be neglected. Second, the rotifers have an average digestion transit time of 1200 seconds. Since the fluospheres are not metabolized by the rotifers, they are ejected back into the sample by the rotifer after 1000 seconds, which may contribute to an increase in bead concentration.

For the test sample the concentration of fluospheres decreases slightly with a slope corresponding to an ingestion rate per organism of $10^{-3}$ beads/sec. Here, the feeding rate was reduced by a factor of 30 from exposure to 1 ppm of diazanon.

Figure 7C:
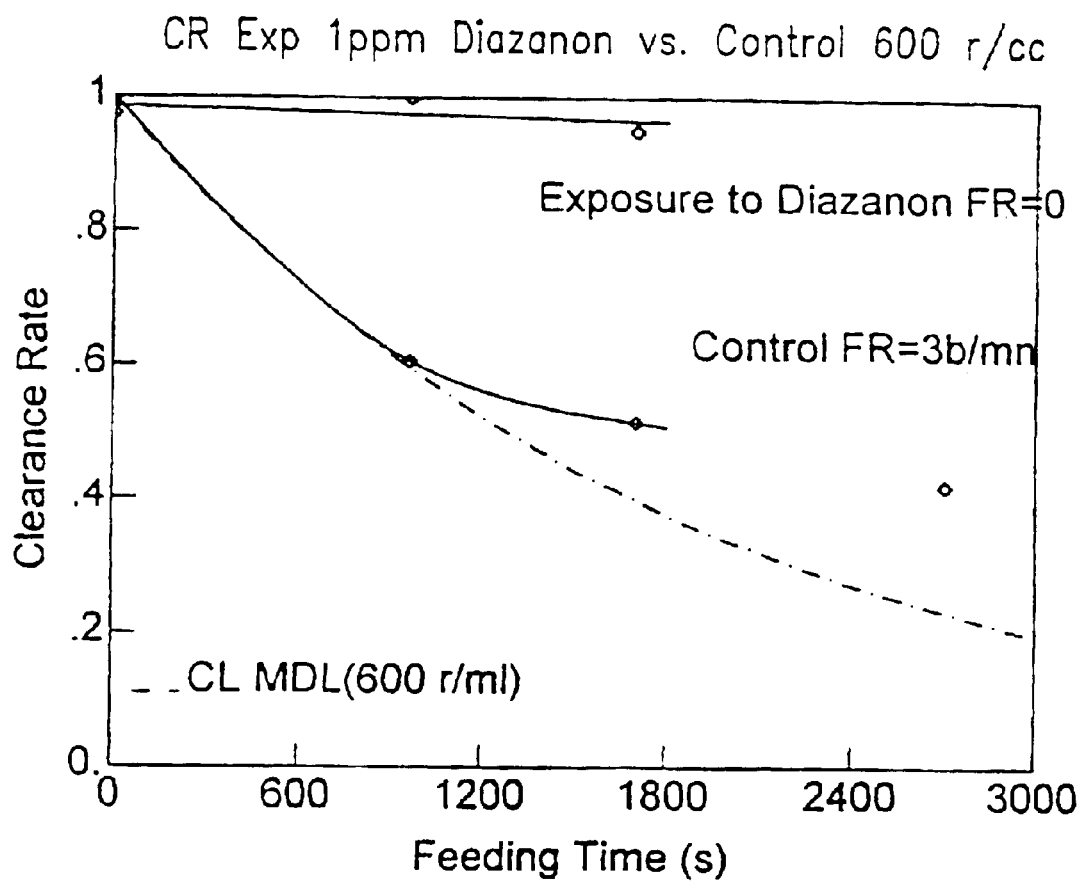
FIG. 7C shows normalized fluosphere concentrations versus feeding time for a test sample containing 1 ppm of diazanon and a control sample, using a rotifer concentration of 600 rotifers/ml.

FIG. 7C shows normalized fluosphere concentrations versus feeding time for a test sample containing 1 ppm of diazanon and a control sample. The concentration of organisms is now 600 rotifers/ml.

Again, for the control sample, the agreement between model and experiment is excellent for the first 600 seconds. The feeding rate is now 3 beads/min per organism, compared well to the 1.7 beads/min per organism value obtained earlier. For the test sample, the concentration of beads remains almost unchanged with time and indicates a feeding rate of less than 0.05 beads/min. This measurement is consistent with previous experiments.

FIG. 7D shows normalized fluosphere concentrations versus feeding time for a 600 rotifers/ml sample and an 1000 rotifers/ml sample. The two samples are exposed to concentrated 2 $\mu$m fluospheres for 1700 seconds. The fluosphere concentrations are monitored continuously and the normalized concentrations are reported and compared to the clearance rate model described earlier. The agreement between model and experiment is optimum for an average feeding rate per organism equal to 4.8 beads/min.

To express feeding rate in terms of mass, the following equation may be used:

$$\dot{M} = FR \cdot \rho \cdot V_{fluo} \qquad \text{(Eq. 12)}$$

where FR, $\rho$, and $V_{fluo}$ are the average feeding rate per individual rotifer, the fluosphere density, and the individual fluosphere volume, respectively. Here, for a feeding rate of 4.8 beads/min and spherical fluospheres with a density of 1.055 g/ml and a diameter of 2 $\mu$m, M-dot=21×10$^{-12}$ g/min per organism.

The foregoing description of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A device for detecting a microparticle in a fluid, the microparticle being tagged with a fluorescent substance, the fluorescent substance emitting fluorescent light of predetermined wavelengths when exposed to electromagnetic radiation, the device comprising:

a capillary tube having an internal diameter configured to admit the microparticles one at a time;

a fluid delivery system coupled to the capillary tube, the fluid delivery system capable of causing the microparticle and the fluid to flow through the capillary tube;

a source of electromagnetic radiation for projecting a beam of electromagnetic radiation of predetermined wavelength and size of the capillary tube through said capillary tube whereby the beam size and the interior of the capillary tube define a test volume which exposes the fluorescent substance in the test volume to the electromagnetic radiation to cause emission of fluorescent light by said fluorescent microparticles in said volume;

a detection device configured and disposed to detect fluorescent light emitted from the fluorescent substance in the volume when the microparticle is in the capillary volume and provide an output signal; and means disposed between said fluorescent substance in said volume and the detector to pass light at said predetermined wavelengths.

2. The device of claim 1, wherein said fluid delivery system transports the microparticles through said volume at a substantially uniform velocity.

3. The device of claim 1 wherein said means disposed between such fluorescent substance in said volume and the detector to pass light at said predetermined wavelengths comprises a diffraction grating and in which the detection device comprises devices for detecting different wavelengths of light provided by said diffraction grating.

4. A device as in claim 3 in which the source of electromagnetic energy comprises a plurality of lasers operating at different wavelengths.

* * * * *

UNITED STATES PATENT AND TRADEMARK OFFICE
CERTIFICATE OF CORRECTION

| | | |
|---|---|---|
| PATENT NO. | : 6,816,257 B2 | Page 1 of 1 |
| APPLICATION NO. | : 10/652665 | |
| DATED | : November 9, 2004 | |
| INVENTOR(S) | : Philippe J. Goix | |

It is certified that error appears in the above-identified patent and that said Letters Patent is hereby corrected as shown below:

ON THE COVER PAGE:

Item (60) under Related U.S. Application Data: replace "60/049,212" with -- 60/049,012 --.

Column 1, line 7, replace "Jul. 7, 2002" with -- Jul. 7, 2000 --.

Column 1, line 10, replace "60/049,292" with -- 60/049,012 --.

Signed and Sealed this

Thirty-first Day of May, 2011

David J. Kappos
*Director of the United States Patent and Trademark Office*